US012758431B2

(12) United States Patent
Sim et al.

(10) Patent No.: US 12,758,431 B2
(45) Date of Patent: Oct. 13, 2026

(54) PLASTER FOR FIXING DRAINAGE TUBE

(71) Applicant: THE CATHOLIC UNIVERSITY OF KOREA INDUSTRY-ACADEMIC COOPERATION FOUNDATION, Seoul (KR)

(72) Inventors: Ji Youn Sim, Seoul (KR); Dong Jin Chang, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 656 days.

(21) Appl. No.: 18/205,728

(22) Filed: Jun. 5, 2023

(65) Prior Publication Data

US 2024/0009037 A1 Jan. 11, 2024

(30) Foreign Application Priority Data

Jul. 11, 2022 (KR) ........................ 10-2022-0084827

(51) Int. Cl.
*A61F 13/0246* (2024.01)
*A61M 1/00* (2006.01)
(Continued)

(52) U.S. Cl.
CPC ........... *A61F 13/0246* (2013.01); *A61M 1/84* (2021.05); *A61M 25/02* (2013.01); *A61M 27/00* (2013.01);
(Continued)

(58) Field of Classification Search
CPC ........ A61F 13/0246; A61F 2013/00412; A61F 5/4405; A61M 1/84; A61M 25/02;
(Continued)

(56) References Cited

U.S. PATENT DOCUMENTS 4,316,461 A * 2/1982 Marais .................. A61M 5/425 604/179
4,484,913 A * 11/1984 Swauger ................. A61M 5/00 604/179
(Continued)

FOREIGN PATENT DOCUMENTS

KR 20-0489503 Y1 6/2019

*Primary Examiner* — Wesley G Harris
(74) *Attorney, Agent, or Firm* — Bridgeway IP Law Group, PLLC; Sang Ho Lee; Hyun Woo Shin

(57) ABSTRACT

A plaster for fixing a drainage tube is provided, which fixes the drainage tube that is inserted into a patient's body and discharges liquid inside the patient's body to the outside of the patient's body. The plaster includes a plurality of support pads attached to the patient's body to be spaced apart from each other, each of the plurality of support pads having a certain thickness; a support band fixed to respective upper surfaces of the support pads to cover the skin; and a plurality of holders detachably coupled to an upper surface of the support band to hold and fix the drainage tube. The plaster for fixing a drainage tube maintains a stable fixation state by blocking longitudinal movement of the drainage tube as well as lifting of the drainage tube, and protects the skin from a 3-way valve to prevent pain even when the skin is pressed.

14 Claims, 10 Drawing Sheets

(51) Int. Cl.
*A61M 25/02* (2006.01)
*A61M 27/00* (2006.01)
*A61M 39/10* (2006.01)
*A61M 39/22* (2006.01)
*A61F 13/00* (2006.01)

(52) U.S. Cl.
CPC .......... *A61M 39/10* (2013.01); *A61M 39/223* (2013.01); *A61F 2013/00412* (2013.01); *A61M 2025/0246* (2013.01); *A61M 2025/0266* (2013.01)

(58) Field of Classification Search
CPC .... A61M 27/00; A61M 39/10; A61M 39/223; A61M 2025/0246; A61M 2025/0266; A61M 1/915; A61M 2025/026; A61M 2025/0253
See application file for complete search history.

(56) References Cited

U.S. PATENT DOCUMENTS

| | | | | | |
|---|---|---|---|---|---|
| 4,626,246 | A * | 12/1986 | Verkade | A61M 25/02 | 128/877 |
| 5,018,534 | A * | 5/1991 | Grant | A61M 25/02 | 128/877 |
| 5,037,398 | A * | 8/1991 | Buchanan | A61M 25/02 | 128/DIG. 26 |
| 8,425,467 | B1 * | 4/2013 | Haak | A61M 25/02 | 604/174 |
| 2007/0265571 | A1 * | 11/2007 | Utterberg | A61M 25/02 | 604/174 |
| 2014/0188079 | A1 * | 7/2014 | Simons | A61M 25/02 | 604/179 |
| 2018/0311474 | A1 * | 11/2018 | Tyler | A61B 50/20 | |

* cited by examiner

PLASTER FOR FIXING DRAINAGE TUBE

CROSS-REFERENCE TO RELATED APPLICATION

This application claims priority to Korean patent application No. 10-2022-0084827, filed on Jul. 11, 2022, the entire disclosure of which is incorporated herein by reference.

TECHNICAL FIELD

The disclosure relates to a fixing plaster for fixing a drain tube, and more particularly, to a plaster for fixing a drainage tube, which blocks both lifting and longitudinal movement of the drainage tube, and furthermore, does not cause pressure on the skin, thereby causing no pain and maintaining a good fixation state.

BACKGROUND ART

The drainage tube is a discharging tube for guiding liquid generated in a body cavity to the outside of a body, and is inserted into the body through a separate passage after an incision portion of the body is sutured during surgery. A drainage bag is connected to an end of a drainage tube. The drainage bag accommodates the liquid that escapes through the drainage tube.

Because a drainage tube is a transparent tube made of synthetic resin and has flexibility, the drainage tube can be easily bent according to a patient's movement or posture change. When the drainage tube is bent, liquid cannot pass therethrough, and, when time passes without discovering the fact that the drainage tube is bent, bacteria may proliferate in the liquid stagnant in the body, and the pressure in the body may rise, causing the surgical site to burst.

In installation of the drainage tube, it is important to fix the drainage tube so that it does not come off. There are several methods of fixing a drainage tube, one of them is a method of fixing a drainage tube by knotting a surgical suture to the drainage tube. However, in the method of fixing a drainage tube by using a suture, the drainage tube cannot be firmly fixed. For this reason, other fixing means instead of sutures have been proposed.

As a background technology of the invention related thereto, a drainage tube fixing member has been disclosed in Korean Utility Model Registration No. 20-0489503.

The disclosed invention relates to a drainage tube fixing member for fixing a drainage tube inserted into a human body to remove drainage and inflammatory exudate generated during wound healing after surgery, the drainage tube fixing member including an attachment fixing part attached to a patient's surgical site and a drainage tube fixing part coupled to the attachment fixing part to fasten and fix a drainage tube exposed to the outside of the human body. The drainage tube fixing part includes a guide support portion coupled to the attachment fixing part to selectively support a vertical or horizontal state of the drainage tube, and a fastening portion fastened to the guide support portion to maintain a vertical or horizontal state and configured to fasten and support the drainage tube exposed to the outside of the human body. The guide support portion includes a lower support coupled to the attachment fixing part and having a cutout portion wider than the outer diameter of the drainage tub at the center of the lower support, and a fastening portion support extending upwards from each side of the cutout portion to fasten and support the fastening portion and having a guide hole formed from a lower portion of the extension to an upper portion thereof to have a '¬' shape.

Conventional general drainage tube fixing devices have insufficient designs for pressing. For example, a component part included in a drainage tube, such as a 3-way valve, may press the skin and cause pain, but conventional general drainage tube fixing devices do not have a structure for preventing such pressure.

DESCRIPTION OF EMBODIMENTS

Technical Problem

Provided is a plaster for fixing a drainage tube, which maintains a stable fixation state by blocking longitudinal movement of the drainage tube as well as lifting of the drainage tube.

Solution to Problem

According to an embodiment of the disclosure, a plaster for fixing a drainage tube fixes the drainage tube that is inserted into a patient's body and discharges liquid inside the patient's body to the outside of the patient's body, and includes a plurality of support pads attached to the patient's body to be spaced apart from each other, each of the plurality of support pads having a certain thickness; a support band fixed to respective upper surfaces of the support pads to cover the skin; and a plurality of holders detachably coupled to an upper surface of the support band to hold and fix the drainage tube.

The drain tube includes a flexible tube, a 3-way valve, and connectors that connect the 3-way valve to the flexible tube, and the support band has a support that supports the 3-way valve and the connectors and separates the 3-way valve and the connectors from the skin.

The connectors are located on opposite sides with the 3-way valve interposed between the connectors, and restraining protrusions that contact the connectors and prevent movements of the connectors are formed on both ends of the support, respectively.

Each of the support pads is a sheet-type member having a certain thickness, and the support band is detachably coupled to the respective upper surfaces of the support pads through adhesive cloths.

A protective housing that covers and protects the 3-way valve supported by the support is detachably mounted on the support.

The support has a rectangular shape having a certain width and a certain thickness, and the protective housing includes an elastic plate that has a bent shape and is elastically deformed; and an outer shell that covers the elastic plate and has both ends detachably coupled to the support and an access hole corresponding to the 3-way valve.

A stretchable portion acting to increase a length of the support band when a tensile force is applied to the support band is formed on the support.

A valve groove for accommodating the 3-way valve and suppressing a movement of the 3-way valve is formed in the support.

Each of the holders includes a folding sheet having a certain thickness, being foldable, and accommodating the connector in a folded state; and a folding holding portion mounted on the folding sheet to maintain a state in which the folding sheet is folded.

The folding sheet is equipped with a friction cushion for preventing the connector from slipping.

The folding sheet includes an elastic sheet for imparting elasticity to the folding sheet.

Effects of Disclosure

A plaster for fixing a drainage tube according to the disclosure as described above maintains a stable fixation state by blocking longitudinal movement of the drainage tube as well as lifting of the drainage tube, and protects the skin from a 3-way valve to prevent pain even when the skin is pressed.

DETAILED DESCRIPTION

An embodiment of the disclosure will now be described in more detail with reference to the accompanying drawings.

A plaster for fixing a drainage tube according to an embodiment to be described later maintains a stable fixation state by blocking both lifting and longitudinal movement of the drainage tube inserted into a patient's body.

For reference, the drainage tube includes a flexible tube having one end inserted into the patient's body and the other end to which a drainage bag is connected, a 3-way valve installed in the middle of the flexible tube, and a connector for connecting the 3-way valve to the flexible tube. Two of the three ports of the 3-way valve are connected to the flexible tube through the connector.

Figure 1:
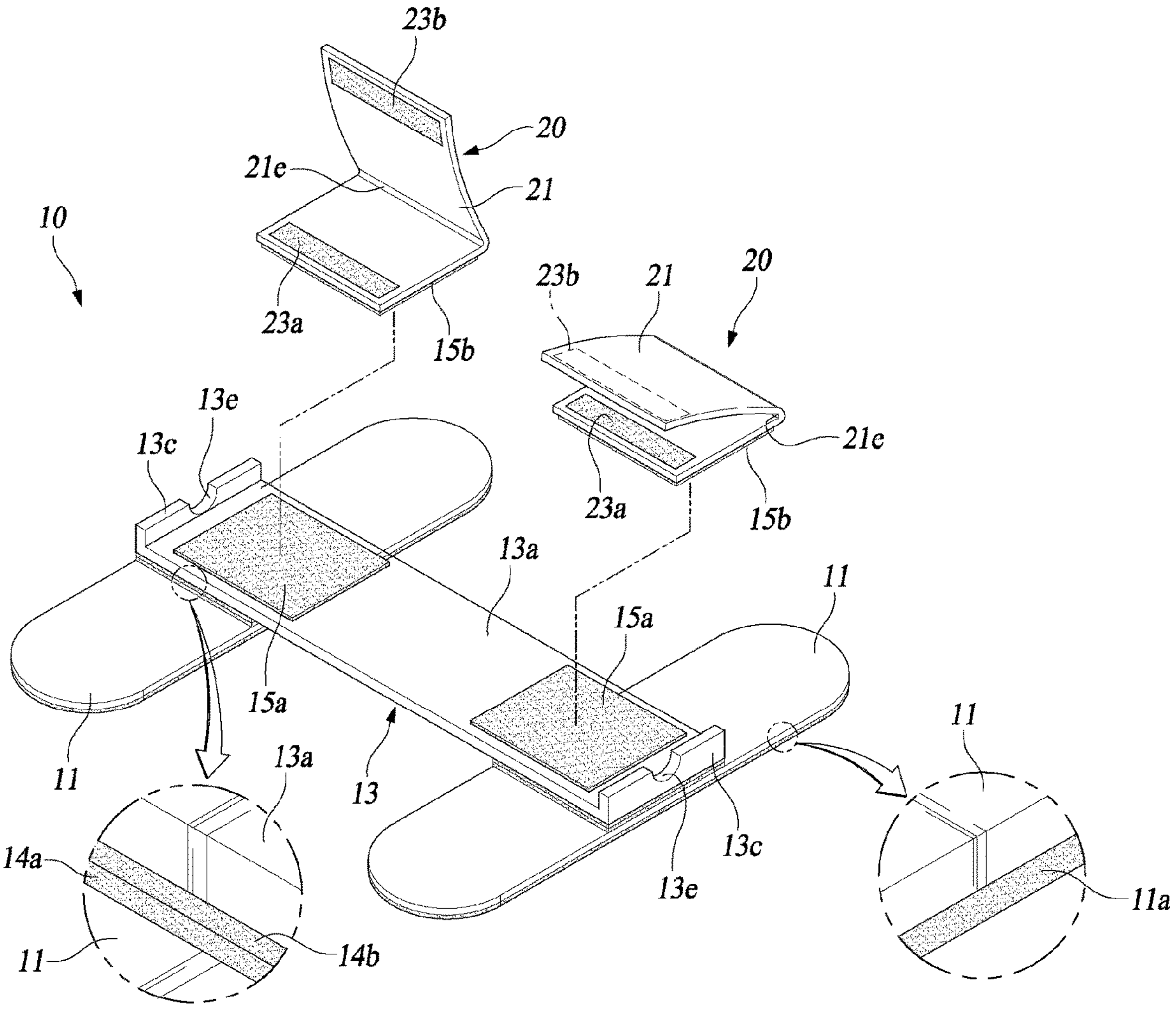
FIG. 1 is an exploded perspective view of a plaster for fixing a drainage tube according to an embodiment of the disclosure.
Figure 2:
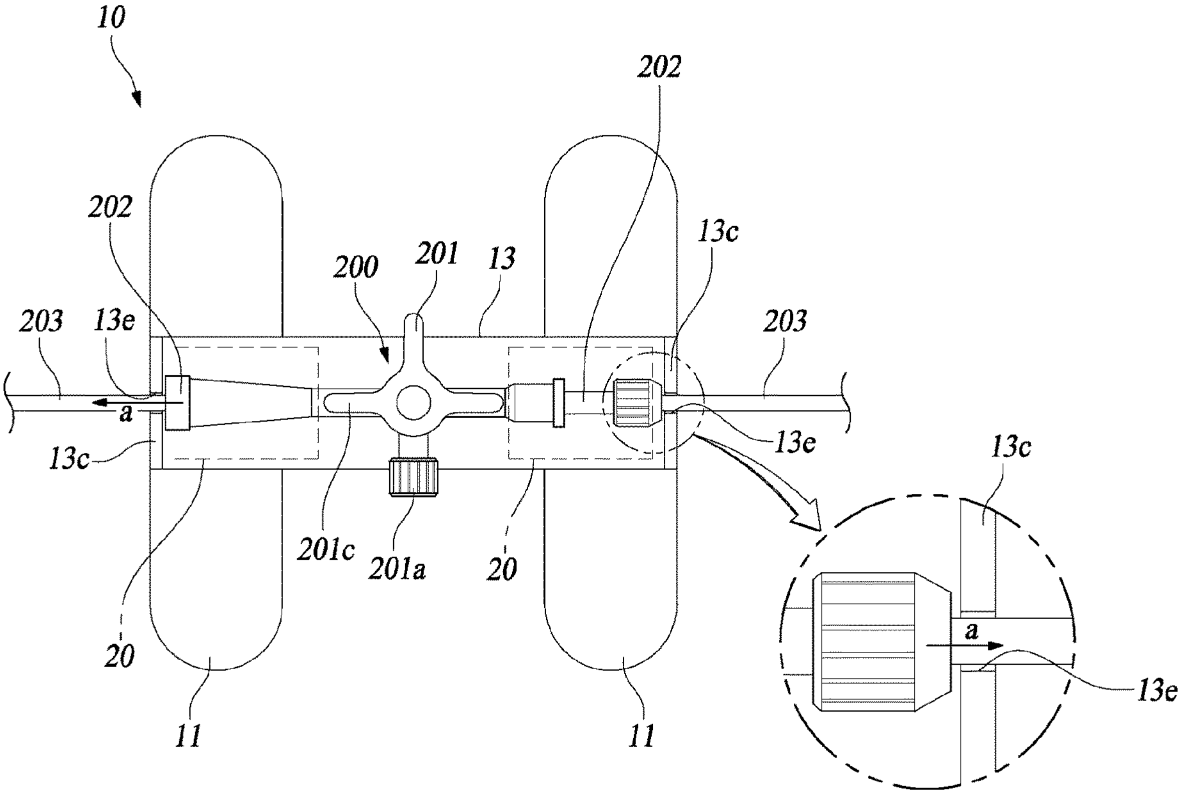
FIG. 2 is a plan view schematically showing a drainage tube mounted on the plaster shown in FIG. 1.

FIG. 1 is an exploded perspective view of a plaster 10 for fixing a drainage tube according to an embodiment of the disclosure, and FIG. 2 is a plan view schematically showing a drainage tube mounted on the plaster 10 shown in FIG. 1.

As shown in the drawings, the plaster 10 according to the present embodiment has a pair of support pads 11, a support band 13, and two holders 20.

Each of the support pads 11 is a sheet-type member that is adhesively fixed to the patient's skin and has a certain thickness, and has an adhesive foam **11*a* on its bottom surface. The adhesive foam 11*a* maintains the adhesion state of the support pad 11. The support pad 11 has flexibility and thus may closely adhere to the patient's skin. The shape or size of the support pad 11** may vary.

An adhesive cloth **14*a* is fixed onto an upper surface of the support pad 11. The adhesive cloth 14*a* is a member attached to an adhesive cloth 14*b* on a bottom surface of the support band 13, which is to be described later. Velcro fabric may be used as the adhesive cloths 14*a* and 14*b*. However, snap buttons may be applied instead of the adhesive cloths 14*a* and 14*b***.

The support band 13 is a member having both ends detachably fixed to the upper surface of the support pad 11 and configured to cover the skin. The material of the support band 13 is the same as that of the support pad 11.

The support band 13 has a support **13*a* and restraining protrusions 13*c***.

The support **13*a* takes the shape of a rectangular plate having a certain thickness, and, as shown in FIG. 2, supports a 3-way valve 201 and connectors 202 and separates them from the skin. A reason for supporting the 3-way valve 201 and the connectors 202 is to prevent the 3-way valve 201 and the connectors 202 from pressing on the skin and causing pain. When there is no support 13*a*, the 3-way valve 201** may cause injury or pain by pressing the skin.

The adhesive cloths **14*b* are fixed onto respective lower surfaces of both ends of the support 13*a*. As described above, the adhesive cloths 14*b* are members attached to the adhesive cloths 14*a* provided on the support pads 11. Adhesive cloths 15*a* are provided on respective upper surfaces of both ends of the support 13*a*. The adhesive cloths 15*a* correspond to adhesive cloths 15*b* fixed to the holders 20**, respectively.

The restraining protrusions **13*c* are formed at both ends of the support 13*a*, come into contact with the connectors 202, and prevent movement of the connectors 202. In other words, the connectors 202 on both sides are prevented from departing in a direction indicated by arrow a. Movement of a drainage tube 200 in a longitudinal direction is prevented by the restraining protrusions 13*c*. The longitudinal direction refers to an extension direction of a flexible tube 203**.

Accommodation grooves **13*e* are provided in the restraining protrusions 13*c*, respectively. The accommodation grooves 13*e* are grooves onto which the flexible tube 203 is fit. As the flexible tube 203 is fit onto the accommodation grooves 13*e*, the flexible tube 203** does not shake in left and right directions.

The holders 20 are members detachably coupled to the upper surface of the support band 13. For example, each of the holders 20 has a structure in which a rectangular sheet is folded about a folding line **21*e*, and accommodates each of the connectors 202** therebetween.

The holder 20 includes a folding sheet 21 and adhesive cloths **23*a* and 23*b*. The folding sheet 21 is a flexible synthetic resin member that is folded or unfolded about the folding line 21*e*. The folding sheet 21 adheres to the connector 202** in a folded state and constrains the connector therein.

The adhesive cloths **23*a* and 23*b* are folding holding portion fixed to a fore end of an inner surface of the folding sheet 21, and maintains a state in which the folding sheet 21 is folded. When the folding sheet 21 is folded with the connector 202 placed thereon and the adhesive cloths 23*a* and 23*b* are attached to each other, fixing of the connector 202 to the holder is completed. As the connector 202 is fixed to the holder 20, there is no lifting of the drainage tube 200. In other words, the drainage tube 200 is not separated from the support band 13**.

An adhesive cloth **15*b* is fixed to the lower surface of the folding sheet 21. The adhesive cloth 15*b* is detachably attached to the adhesive cloth 15*a* of the support band 13**.

Figure 3:
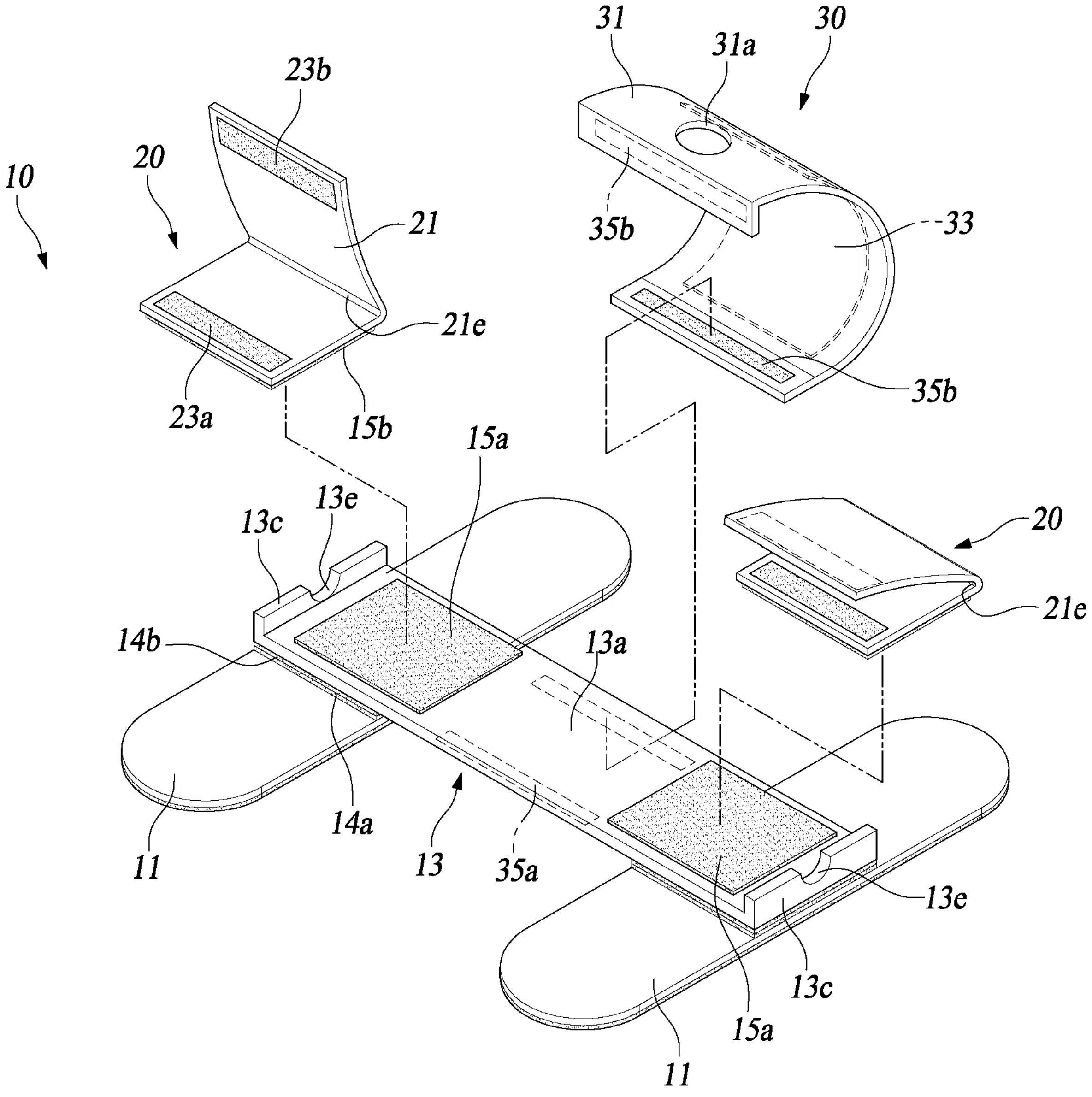
FIG. 3 is an exploded perspective view of a modification of the plaster for fixing a drainage tube according to an embodiment of the disclosure.

FIG. 3 is an exploded perspective view of a plaster 10 for fixing a drainage tube, which is a modification of the plaster

Figure 4:
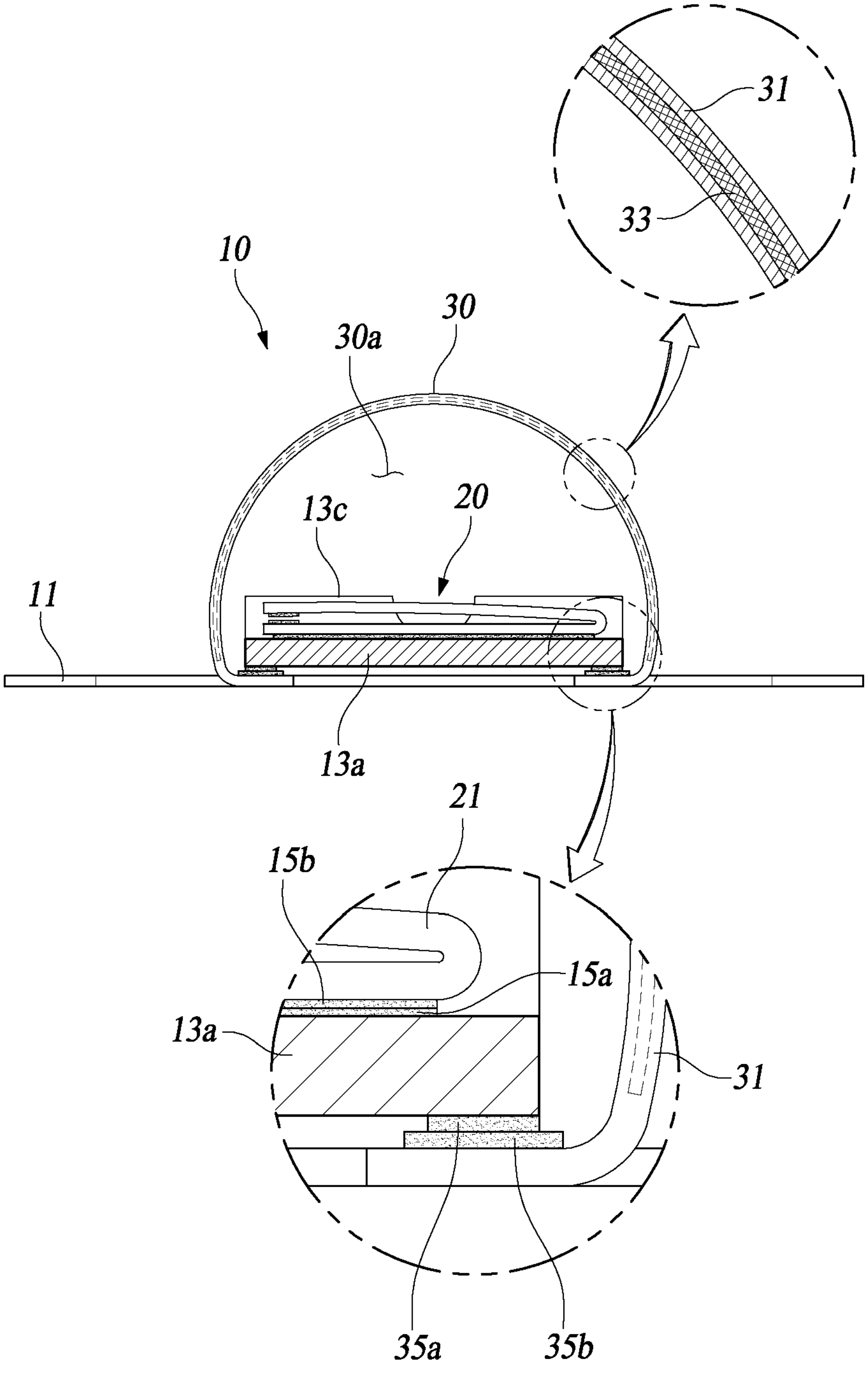
FIG. 4 is a side view of the plaster of FIG. 3.

10 for fixing a drainage tube according to an embodiment of the disclosure. FIG. 4 is a side view of the plaster 10 of FIG. 3.

The same reference numerals as the described-above reference numerals indicate the same members with the same functions.

Referring to the drawings, it may be seen that a protective housing 30 is detachably mounted on the support band 13. The protective housing 30 serves to provide a protective space above the support band 13. A 3-way valve is accommodated in the protective space 30*a*. The reason for accommodating the 3-way valve in the protective space 30*a* is, for example, to prevent a switching lever 201*c* (see FIG. 2) of the 3-way valve from being caught by an external object and turning, while the patient is moving. When the switching lever 201*c* turns abnormally, a drainage passage may be blocked, and bacteria may enter through the 3-way valve.

The protective housing 30 includes an elastic plate 33, an outer shell 31, and adhesive cloths 35*b*. The elastic plate 33 is formed by bending a rectangular plate, and has a substantially C shape in a state where no external force is applied. Of course, the elastic plate 33 may be further bent or unfolded by applying an external force.

The outer shell 31, which is a synthetic resin member surrounding the elastic plate 33, may be manufactured by injection molding. In other words, the outer shell 31 may be manufactured by positioning the elastic plate 33 in a mold and then injecting a resin. The outer shell 31 is provided with an access hole 31*a*. The access hole 31*a*, which is a through hole, exposes a syringe connection port 201*a* (see FIG. 2) of the 3-way valve to the outside. An injection needle may be inserted into the syringe connection port 201*a* through the access hole 31.

The adhesive cloths 35*b* are members fixed to respective inner surfaces of both ends of the outer shell 31, respectively, and are attached to adhesive cloths 35*a* located on the lower surface of the support band 13. The protective housing 30 may be fixed to the support band 13 through the adhesive cloths 35*a* and 35*b*.

Figure 5:
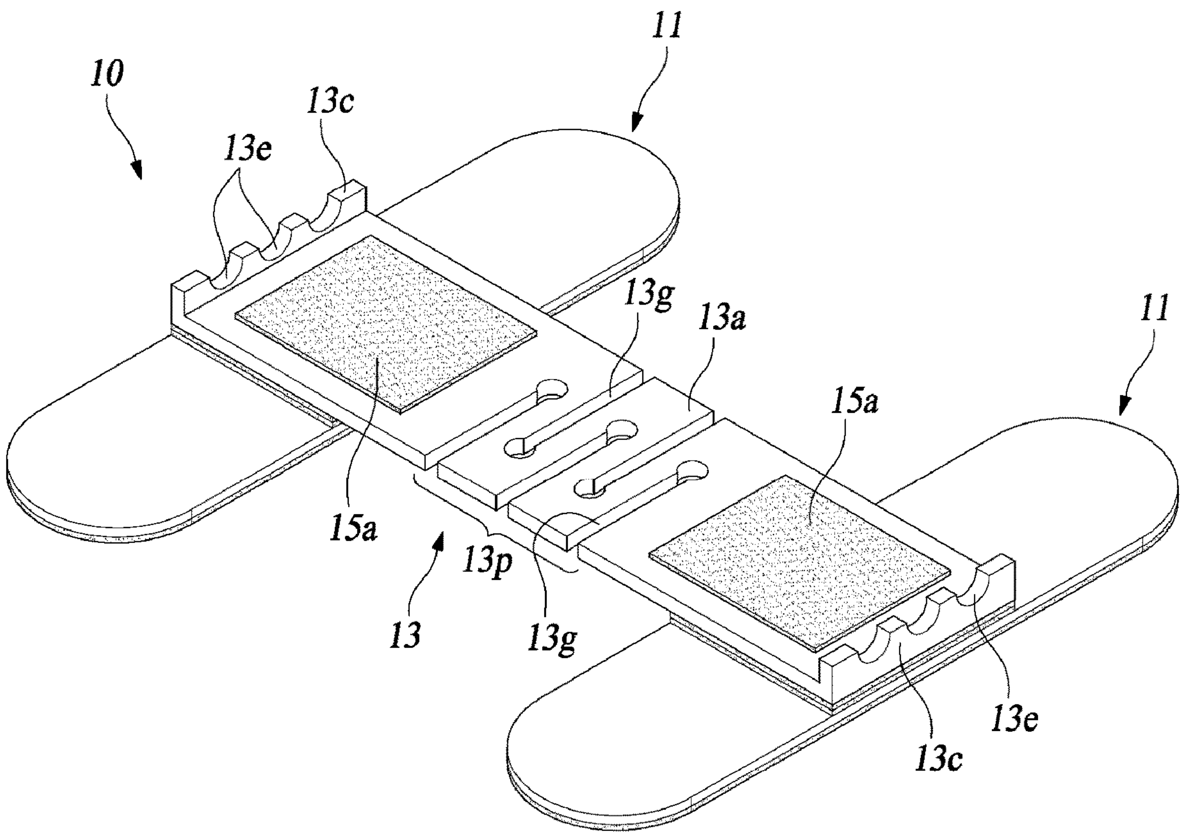
FIGS. 5 through 7 are views showing modifications of a support band in a plaster for fixing a drainage tube according to an embodiment of the disclosure.
Figure 6:
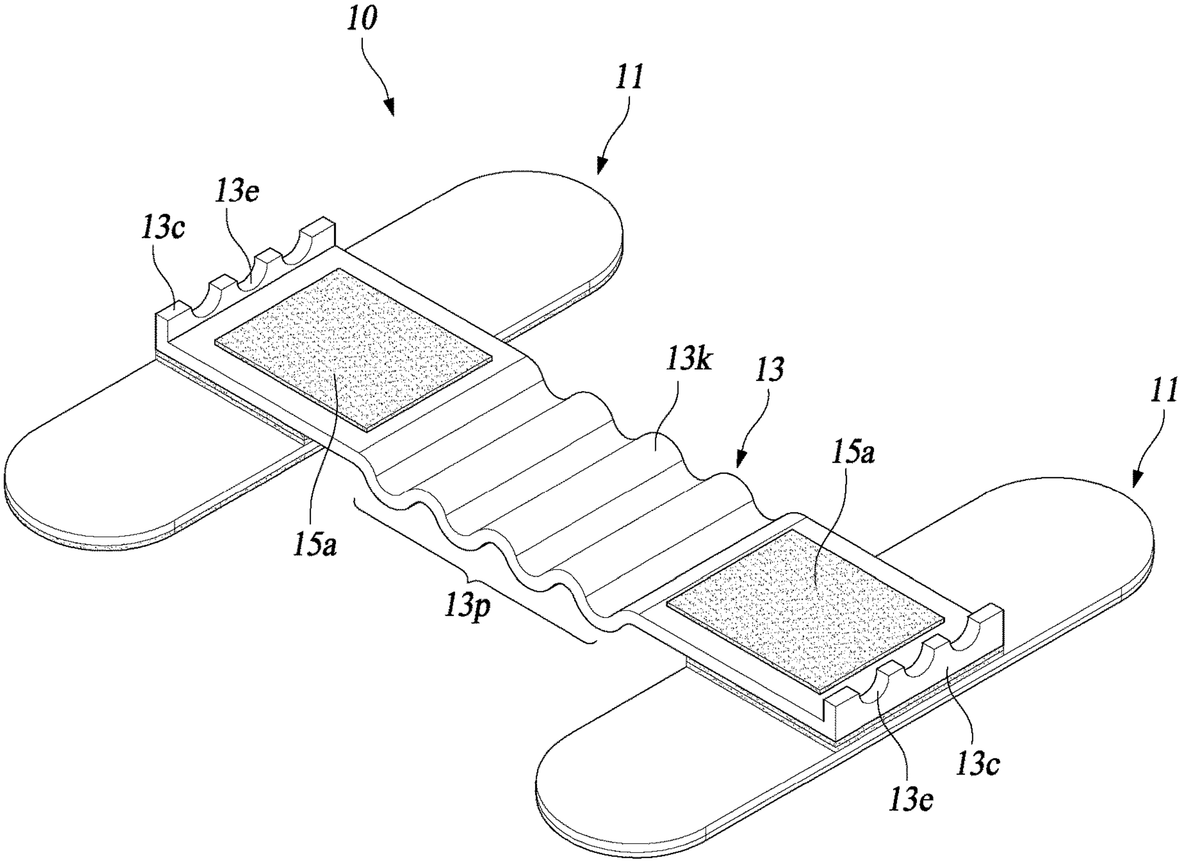
Figure 7:
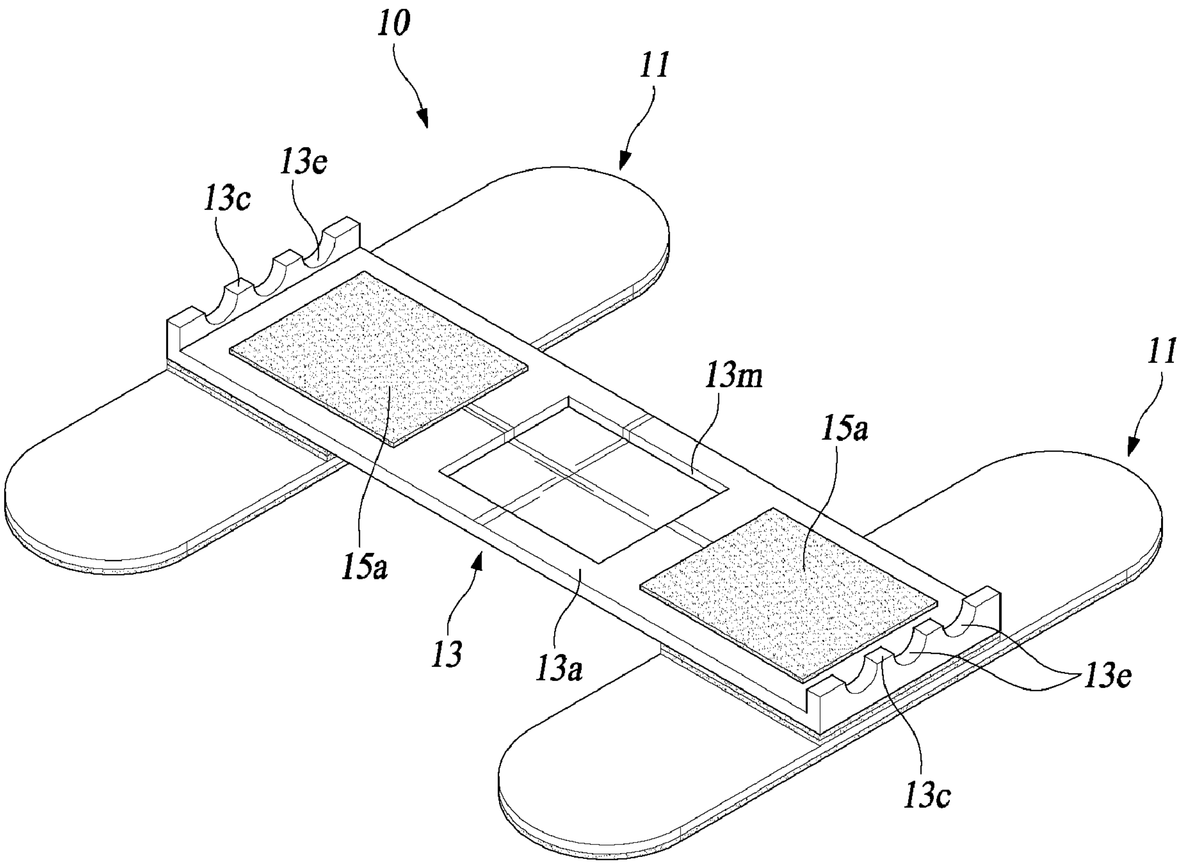

FIGS. 5 through 7 are views showing modifications of the support band 13 in a plaster for fixing a drainage tube, according to an embodiment of the disclosure.

A stretchable portion 13*p* composed of a plurality of slits 13*g* is applied to the supporting band 13 shown in FIG. 5. Each of the slits 13*g* extends in a width direction of the support 13*a*, and the plurality of slits 13*g* are parallel to each other. The slit 13*g* serves to increase the length of the support band 13 when a tensile force is applied to the support band 13. For example, when a distance between the support pads 11 increases according to a movement of the patient, the length of the support band 13 is increased.

The plaster 10 to which the stretchable portion 13*p* is applied is suitable for installation at a joint portion. This is because, whenever a patient bends a joint, the distance between the support pads 11 increases and thus tension is applied to the support band 13.

Three accommodation grooves 13*e* are provided in each restraining protrusion 13*c*. Of course, a desired accommodation groove among the three accommodation grooves 13*e* is used.

In FIG. 6, elastic pleats 13*k* are applied as the stretchable portion 13*p*. The elastic pleats 13*k* have a wavy pattern and increase in length when a tensile force is applied to the support band 13.

A valve groove 13*m* is formed in the support 13*a* of the supporting band 13 shown in FIG. 7. The valve groove 13*m* accommodates the 3-way valve 201, and more stably restrains the 3-way valve 201. In addition, a protrusion height of the 3-way valve 201 may be reduced by applying the valve groove 13*m*. In other words, the height of the 3-way valve 201 relative to the upper surface of the support 13*a* is lowered. Due to this lowering of the height of the 3-way valve 201, the probability that the 3-way valve 201 is caught by an external object when a patient moves is reduced.

Figure 8:
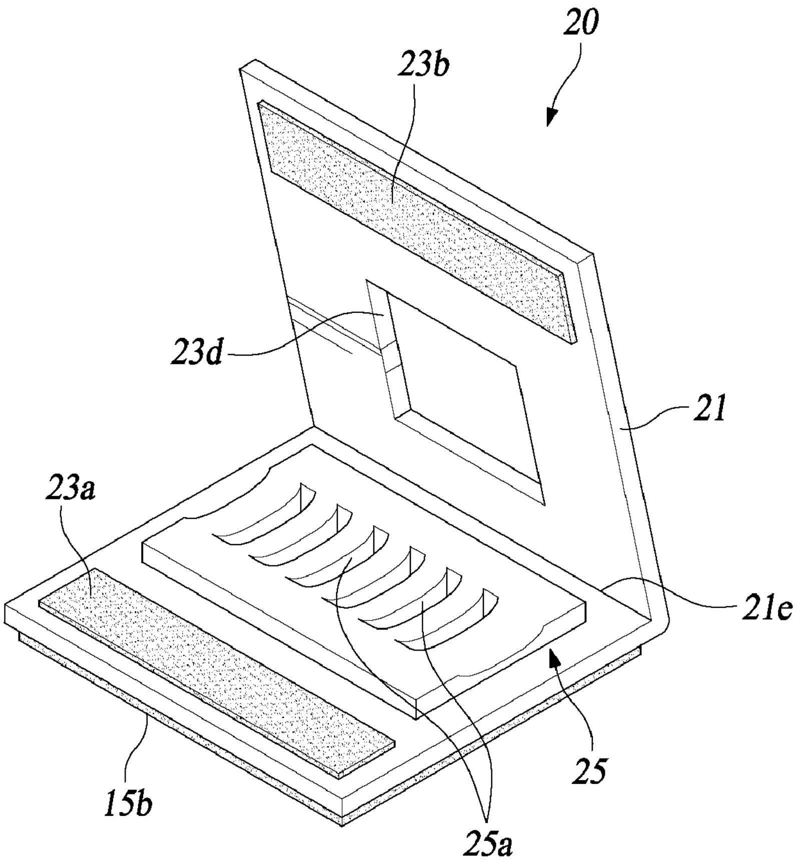
FIGS. 8 through 10 are perspective views of holders applicable to a plaster for fixing a drainage tube according to an embodiment of the disclosure.
Figure 9:
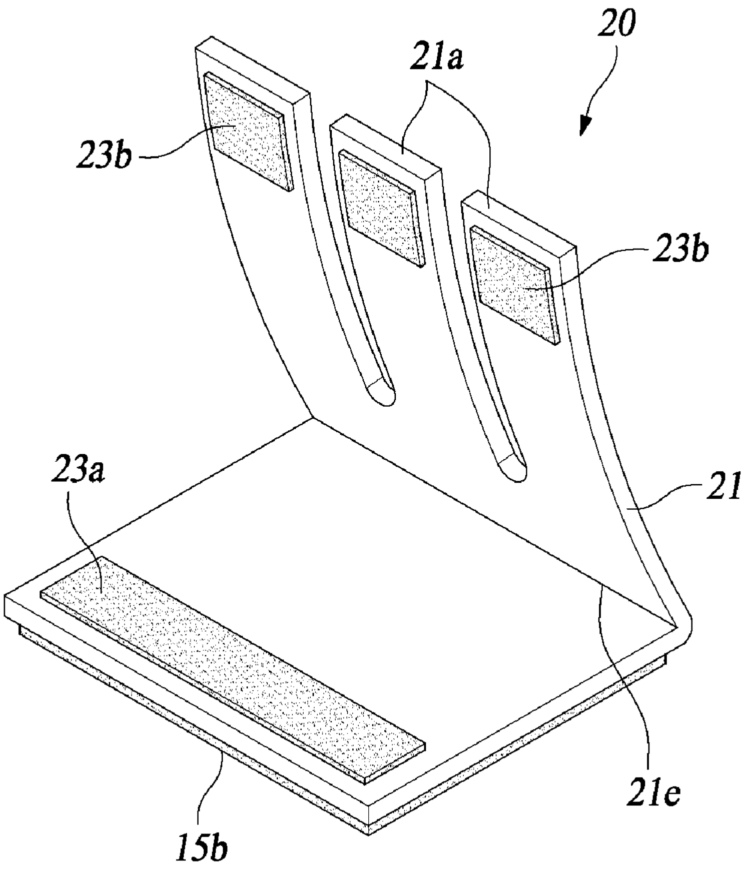
Figure 10:
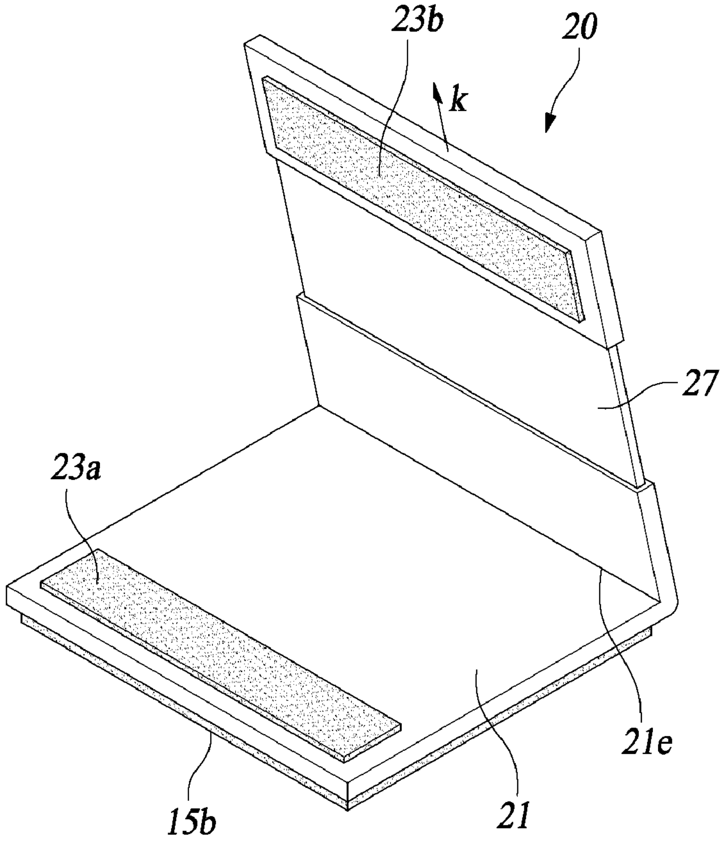

FIGS. 8 through 10 are perspective views of holders 20 applicable to the plaster 20 for fixing a drainage tube according to an embodiment of the disclosure.

The holder 20 shown in FIG. 8 has a friction cushion 25 on one side. The friction cushion 25 is a member made of soft silicon, and has a plurality of locking grooves 25*a*. The friction cushion 25 serves to more stably fix the connector 202. For example, even when the flexible tube 203 is pulled from the outside, the connector 202 does not slip out of the holder 20 due to friction with the friction cushion 25. The locking grooves 25*a* double the fixing force of the connector 202. When a protrusion is formed on a connector depending on the type of connector, the locking grooves 25*aa* provide a more powerful fixing force by accommodating the protrusion.

The other side of the folding sheet 21 is provided with a confirmation hole 23*d*. The confirmation hole 23*d* opens a connection portion between the connector 202 and the flexible tube 203 upward. Through the confirmation hole 23*d*, it may be visually confirmed whether the connector 202 and the flexible tube 203 are normally connected to each other or whether they are about to be disconnected from each other.

In the holder 20 of FIG. 9, one side portion of the folding sheet 21 is divided into three branches. The three branches, which are separation tabs 21*a*, more precisely fix the connector 202. For example, when there are many irregularities on an outer circumferential surface of the connector 202, the separation tabs 21*a* are coupled to concave portions of the irregularities other than convex portions thereof.

An elastic sheet 27 is applied to the holder 20 shown in FIG. 10. The elastic sheet 27 is a rubber or silicon sheet that is elastically deformed by an external force, and stretches when the folding sheet 21 is pulled in a direction indicated by arrow k. Due to this application of the elastic sheet 27 that is elastically deformable, the connector 202 having a large diameter may be fixed without any problems.

While the disclosure has been particularly shown and described with reference to exemplary embodiments thereof, it will be understood by those of ordinary skill in the art that various changes in form and details may be made therein without departing from the spirit and scope of the disclosure as defined by the following claims.

DESCRIPTION OF REFERENCE NUMERALS

10: plaster for fixing
11: support pad
11a: adhesive foam
13: support band
13a: support
13c: restraining protrusions
13e: accommodation grooves
13g: slits
13k: elastic pleats
13m: valve groove
13p: stretchable portion
14a, 14b: adhesive cloths -continued

|  |
|---|
| 15a, 15b: adhesive cloths |
| 20: holder |
| 21: folding sheet |
| 21a: separation tabs |
| 21e: folding line |
| 23a, 23b: adhesive cloths |
| 23d: confirmation hole |
| 25: friction cushion |
| 25a: locking grooves |
| 27: elastic sheet |
| 30: protective housing |
| 30a: protective space |
| 31: outer shell |
| 31a: access hole |
| 33: elastic plate |
| 35a, 35b: adhesive cloths |
| 200: drainage tube |
| 201: 3-way valve |
| 201a: syringe connection port |
| 201c: switching lever |
| 202: connector |
| 203: flexible tube |

The invention claimed is:

1. A plaster configured to fix a drainage tube, which includes a flexible tube, a three-way valve, and connectors located on opposite sides of the three-way valve to connect the three-way valve to the flexible tube, and is configured to be inserted into a patient's body and discharges liquid inside the patient's body to an outside of the patient's body, the plaster comprising:

a plurality of support pads attached to the patient's body to be spaced apart from each other, each of the plurality of support pads having a certain thickness;

a support band fixed to respective upper surfaces of the plurality of support pads to cover a skin; and a plurality of holders detachably coupled to an upper surface of the support band to hold and fix the drainage tube, wherein the support band includes a support configured to support the three-way valve and the connectors of the drainage tube and separate the three-way valve and the connectors from the skin, and wherein restraining protrusions configured to contact the connectors and prevent movements of the connectors are disposed on both ends of the support, respectively.

2. The plaster of claim 1, wherein each of the plurality of support pads is a sheet-type member having a certain thickness, and the support band is detachably coupled to the respective upper surfaces of the plurality of support pads through adhesive cloths.

3. The plaster of claim 1, wherein a protective housing that covers and protects the three-way valve supported by the support is detachably mounted on the support.

4. The plaster of claim 3, wherein the support has a rectangular shape having a certain width and a certain thickness, and the protective housing comprises:

an elastic plate that has a bent shape and is elastically deformed; and an outer shell that covers the elastic plate and has both ends detachably coupled to the support and an access hole corresponding to the three-way valve.

5. The plaster of claim 1, wherein a stretchable portion configured to increase a length of the support band when a tensile force is applied to the support band is formed on the support.

6. The plaster of claim 1, wherein a valve groove configured to accommodate the three-way valve and suppress a movement of the three-way valve is defined in the support.

7. The plaster of claim 1, wherein each of the plurality of holders comprises:

a folding sheet having a certain thickness, being foldable, and configured to accommodate at least one of the connectors in a folded state; and a folding holding portion mounted on the folding sheet to maintain a state in which the folding sheet is folded.

8. The plaster of claim 7, wherein the folding sheet is equipped with a friction cushion for preventing the connectors from slipping.

9. The plaster of claim 7, wherein the folding sheet includes an elastic sheet for imparting elasticity to the folding sheet.

10. A drainage assembly comprising:

a plaster configured to fix a drainage tube, the plaster including:

a plurality of support pads attached to a patient's body to be spaced apart from each other, each of the plurality of support pads having a certain thickness, a support band fixed to respective upper surfaces of the plurality of support pads to cover a skin, and a plurality of holders detachably coupled to an upper surface of the support band to hold and fix the drainage tube; and the drainage tube configured be inserted into the patient's body and discharge liquid inside the patient's body to an outside of the patient's body, the drainage tube including a flexible tube, a three-way valve, and connectors located on opposite sides with the three-way valve to connect the three-way valve to the flexible tube, wherein the support band includes a support that supports the three-way valve and the connectors and separates the three-way valve and the connectors from the skin, and wherein restraining protrusions that contact the connectors and prevent movements of the connectors are disposed on both ends of the support, respectively.

11. The drainage assembly of claim 10, wherein each of the plurality of support pads is a sheet-type member having a certain thickness, and the support band is detachably coupled to the respective upper surfaces of the plurality of support pads through adhesive cloths.

12. The drainage assembly of claim 10, wherein a protective housing that covers and protects the three-way valve supported by the support is detachably mounted on the support.

13. The drainage assembly of claim 12, wherein the support has a rectangular shape having a certain width and a certain thickness, and the protective housing comprises:

an elastic plate that has a bent shape and is elastically deformed; and an outer shell that covers the elastic plate and has both ends detachably coupled to the support and an access hole corresponding to the three-way valve.

14. The drainage assembly of claim 10, wherein each of the plurality of holders comprises:

a folding sheet having a certain thickness, being foldable, and accommodating each of the connectors in a folded state; and a folding holding portion mounted on the folding sheet to maintain a state in which the folding sheet is folded.

* * * * *